United States Patent [19]

Lashmore et al.

[11] Patent Number: 4,699,000

[45] Date of Patent: Oct. 13, 1987

[54] AUTOMATED DEVICE FOR DETERMINING AND EVALUATING THE MECHANICAL PROPERTIES OF MATERIALS

[75] Inventors: David S. Lashmore, Frederick; Jasper L. Mullen, Gaithersburg; Christian E. Johnson, Middletown; Robert S. Polvani, Gaithersburg, all of Md.

[73] Assignee: Micro Properties Inc., Braddock Heights, Md.

[21] Appl. No.: 853,149

[22] Filed: Apr. 17, 1986

[51] Int. Cl.[4] .................. G01N 3/42; G01N 19/00
[52] U.S. Cl. ............................ 73/81; 73/794
[58] Field of Search ............................ 73/81, 794

[56] References Cited

U.S. PATENT DOCUMENTS

| | | | |
|---|---|---|---|
| 2,446,621 | 8/1948 | Thiry | 73/81 X |
| 2,561,266 | 7/1951 | Dietert | 73/81 X |
| 3,805,598 | 4/1974 | Corcoran | 73/81 |
| 4,067,225 | 1/1978 | Dorman et al. | 73/1 DV |
| 4,094,188 | 6/1978 | Bellouin et al. | 73/81 |
| 4,118,975 | 10/1978 | Iwasaki | 73/81 |
| 4,383,450 | 5/1983 | Pringiers et al. | 73/81 X |
| 4,450,713 | 5/1984 | Arimatsu | 73/81 |

OTHER PUBLICATIONS

ASTM Special Technical Publication 889-*Microindentation Techniques in Materials Science & Engineering*, presented Jul. 1984; Characterization of Submicrometre Surface Layers by Indentation, Hubert M. Pollock et al, pp. 47–71; Vickers Indentation Curves of Elastoplastic Material, Jean L. Loubet et al., pp. 72–89; and Indentation Hardness of Surface Coated Materials, Olof Vingsbo et al., pp. 257–271.
*Science of Hardness Testing*; pub. 1973 by American Society for Metals: Chapter 1, pp. 1–11, The Fundamental Basis of the Hardness Test, M. C. Shaw and Chapter 15, pp. 199–211, Hardness Anisotropy in Crystalline Solids, C. A. Brookes et al.
*ASTM Standardization News*; Jan. 1985; pp. 47–51; "Microindentation Hardness Testing"; Robert J. Blau et al.
*Metallurgical Transactions:* vol. 2, Jul. 1971, pp. 1979–1983, The Determination of Yield Strength from Hardness Measurements, J. R. Cahoon et al. and vol. 3, Nov. 1972, p. 3040, The Improved Equation Relating Hardness to Ultimate Strength, J. R. Cahoon.
*Metallurgical Transactions A,* vol. 14A; May 1983; pp. 947–952; "On the Definition of Microhardness; F. G. Yost.
*J. Inst. Metal;* vol. 79, pp. 1–18; pub. 1951; "The Hardness & Strength of Metals"; D. Tabor, Ph.D.
*Fundamentals of Optics,* 3rd ed., McGraw-Hill Book Co.; pub. 1957; pp. 306–307; Francis A. Jenkins et al.
"Stress-Strain Curve for Aluminum in a Continuous Indentation Test"; *Journal of Materials Science;* vol. 12, No. 10, pp. 1961–1965; pub. 1977; W. H. Robinson et al.

*Primary Examiner*—Tom Noland
*Attorney, Agent, or Firm*—James J. Brown

[57] ABSTRACT

A device and method are described for measuring and evaluating mechanical properties such as microhardness of a material. The present invention conveniently incorporates commercially available hardness testing equipment but modifies it to permit continuous evaluation and measurement of the displacement of the stylus used to indent the sample being tested. By simultaneously monitoring displacement, load applied to the stylus and time values relating to the mechanical properties of the material such as wear, fatigue and tensile strength are obtained.

12 Claims, 12 Drawing Figures

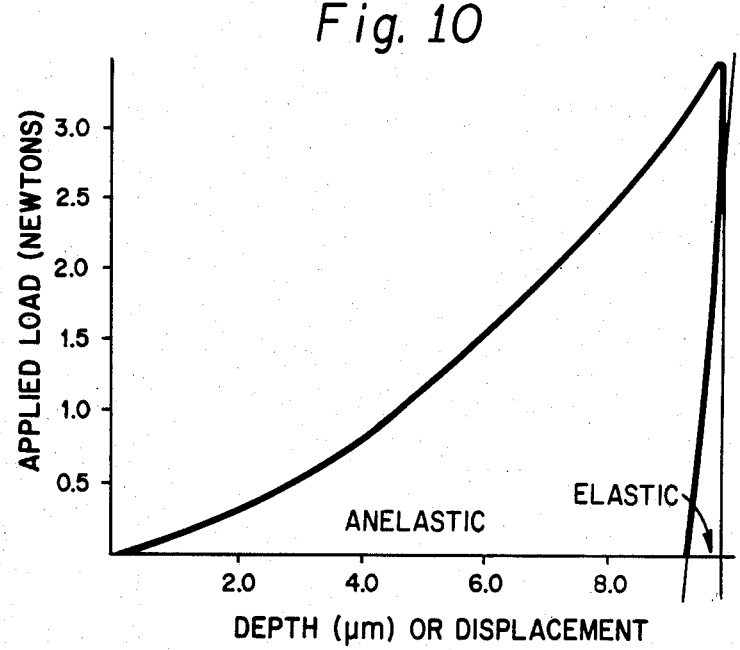
LOAD-DEPTH CURVE FOR FINE
GRAIN POLYCRYSTALINE COPPER
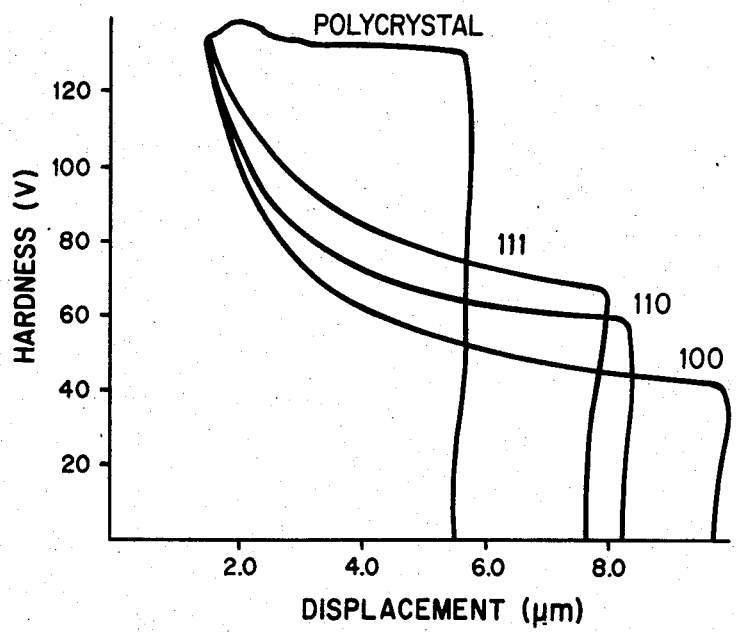
HARDNESS-DEPTH CURVES FOR POLYCRYSTAL AND
THREE ORIENTATIONS OF A COPPER SINGLE CRYSTAL

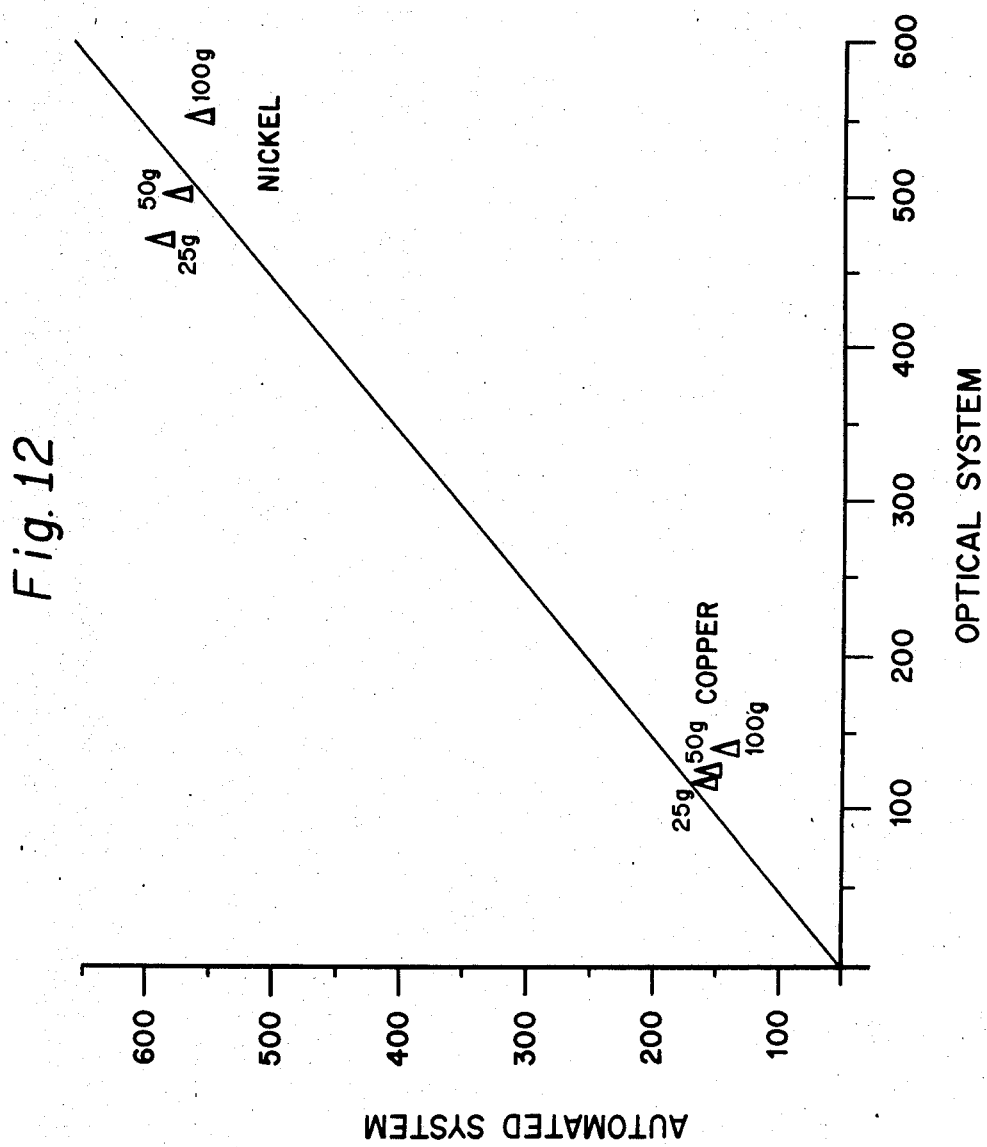

AUTOMATED DEVICE FOR DETERMINING AND EVALUATING THE MECHANICAL PROPERTIES OF MATERIALS

SUMMARY OF THE INVENTION

The present invention relates to an automated device for measuring and evaluating the mechanical properties, such as micro-hardness, of a material. The invention, in particular, is directed to an apparatus and procedures which offer not only significant advances in the measurement of micro-hardness but also yield information relating to the mechanical properties of materials, such as metals, which has not hertofore been available from micro-indentation testing procedures of the prior art.

BACKGROUND OF THE INVENTION

Micro-hardness testing of metals is widely used in industry since, in many cases, hardness values have been found to correlate with physical properties such as wear, fatigue and tensile strength. Micro-hardness testing in the traditional sense involves pressing a diamond indenter, usually a Knoop indenter in the United States or a Vickers indenter in Europe, into a sample which has been polished more or less flat, by means of a static load which is applied to the diamond. After removing the diamond from the surface an impression is left in the sample as a result of plastic deformation which occurs during the indentation process. Optical measurement of the width of this impression then provides data from which the "hardness" of the material can be calculated. The material, it should be noted, also deforms elastically; however, in correct commerical practice this elastic component is very small and is not measured.

Hardness has been defined as the static load applied divided by either the constant area (Vickers) or area of the indenter in contact with the projected surface (Knoop). The Vickers diamond is a tetragonal 136° diamond; the Knoop diamond is an elongated tetrahedron. Therefore, for the Vickers indenter:

$$\text{Hardness} = \frac{2L \sin a/2}{d^2}$$

where d is the average diagonal distance across the indentation, a is 136° and L is the applied load in Kg; and for the Knoop:

$$\text{Hardness} = \frac{L}{l^2 e_p}$$

where L is applied load, l is the length of the long diagonal and ep is a constant related to projected area of the indention.

According to prior art procedures for measuring hardness, an optical microscope is used to measure the width of the indention. This technique imposes a limitation on the accuracy of the measurement as the resolution of an optical microscope is:

$$\Delta l = \frac{\lambda}{2 NA}$$

where $\lambda$ is the wave length of light and NA is a numerical aperture, as defined for example in *Fundamentals of Optics*, Jenkins and White, McGraw-Hill, 1957, pp. 306–307. For microscopes now typically in use, $\Delta l$ is approximately 500 nm.

Accordingly, instruments and techniques of the prior art are inherently subject to error due to the limitations of optical measurement as well as errors in calibration standards, load overshoot and vibration.

It is therefore an object of this invention to provide a system for determining the hardness of a material such as a metal which avoids many of the deficiencies inherent in the prior art by continuously monitoring and registering the displacement of the indenter used to impress the sample. It is a further object of this invention to provide a system for continuously and automatically monitoring and correlating data relating to load applied to the indenter, time and displacement to obtain additional information on mechanical properties of the material.

DISCUSSION OF THE PRIOR ART

U.S. Pat. No. 4,450,713 to Arimatsu, shows a hardness tester for detecting the displacement of the feeler of a hardness tester in terms of a variation in voltage. An evaluation unit converts the voltage variation into a digital signal for hardness, however there is no provision for simultaneously measuring and correlating time and load.

U.S. Pat. No. 3,805,598 to Corcoran, shows an indenter arranged to penetrate a sample. A core moving relative to winding produces an electrical signal analogous to the depth of penetration.

BRIEF DESCRIPTION OF THE DRAWINGS

FIG. 10 is a load-depth curve for fine grain polycrystalline copper.

FIG. 11 is a group of hardness-depth curves for a polycrystal and three orientations of a copper single crystal.

FIG. 12 compares scatter in automated and optical systems.

DESCRIPTION OF THE INVENTION

Figure 1:
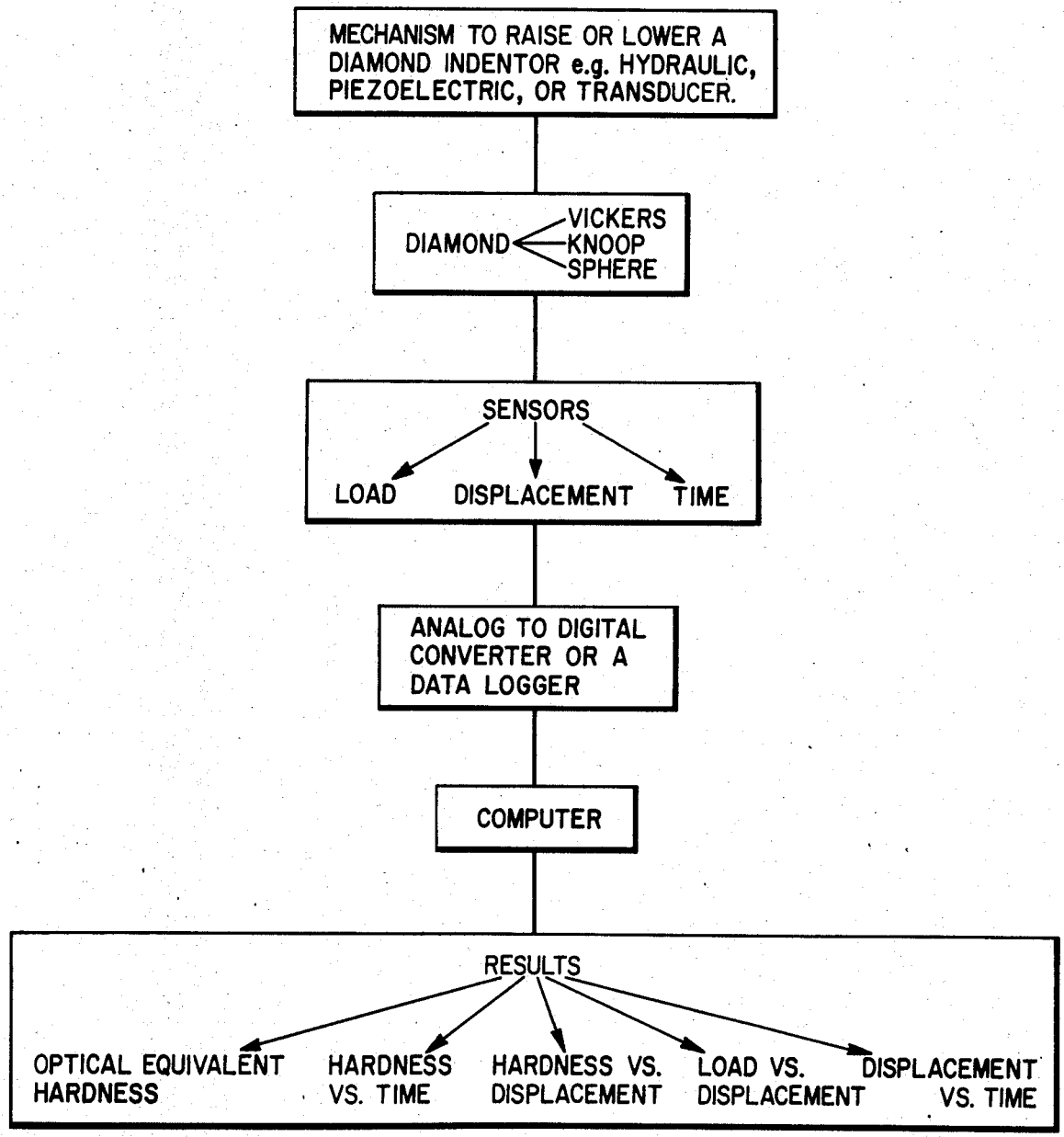
FIG. 1 is a schematic representation of the device of the present invention.

In accordance with the present invention many of the limitations inherent in the prior art are avoided by continuously recording both the applied load and displacement of a stylus which indents the material sample instead of optically measuring the magnitude of the indention and advantage made of the known geometry of the diamond to enable calculation of not only hardness but information on modulus, yield stress, impact, hardness (or strength), creep, and fatigue can now be determined.

The present invention permits measurements to be made of the displacement of the indenter as a function of time both before it hits the sample which it is penetrating and immediately after it has lifted off the sample. Alternative embodiments of the invention employ measurements of the actual load applied to the sample during the deformation or indentation process. All embodiments of the invention involve measurement of time elapsed during indentation. This latter provision involves sampling the load and/or displacement data at fixed times which can be as fast as 0.1 micro-seconds.

The system of the invention is thus able to provide information on instantaneous hardness as a function of displacement of the indentor into the sample, load as a function of displacement or even to obtain information on impact effects. The advantages of this type of a mechanical properties testing system are: (1) the measurement is made on a very small sample of the material which is important to those interested in alloy development or in measuring properties of coatings; (2) the measurement is operator independent; and (3) microhardness and any of these properties can all be done simultaneously.

The device of the invention can employ a commercial, oil damped hardness testing instrument such as a Wilson Tukon Model 300-BM Microhardness Tester as the actual mechanism for applying a diamond indenter to the sample being tested with appropriate modifications in accordance with the invention as described herein. Essentially, the device of this invention requires the following elements:

A stage for holding an essentially flat sample of material. A stylus mounted on one end of a lever arm to vertically impinge on the sample when the stylus is displaced downward; a load mounted on the lever arm above the stylus; an activator for controlling downward displacement of the stylus; devices for simultaneously measuring time of displacement, distance of displacement and load being applied to the stylus when it is impinging on the sample; and instrumentation for receiving and correlating signals generated by the measuring means to produce values relating to the hardness of the material.

Typically, the applied load is measured by a load cell of known type and the vertical displacement of the stylus is measured by a capacitor probe mounted to monitor movement of either the stylus directly or the arm to which it is attached. Signals generated by the load cell and capacitor probe are fed to an analog/digital converter such as a TM-AD212 S-100 converter with a timer/counter capability. Data from the A/D converter is fed to a standard microcomputer and displayed as desired on a monitor or print-out.

The load cell provides information on when the stylus impacts the surface of the sample and on hardness as a function of depth. The capacitance probe gives precise information on the depth of the stylus' penetration into the sample. Because the geometry of the stylus can be precisely calculated, the actual area of impact can also be calculated thereby permitting determination of hardness.

DETAILED DESCRIPTION OF THE DRAWINGS

The present invention will, however, be more fully appreciated by having reference to the accompanying drawings.

Figure 2:
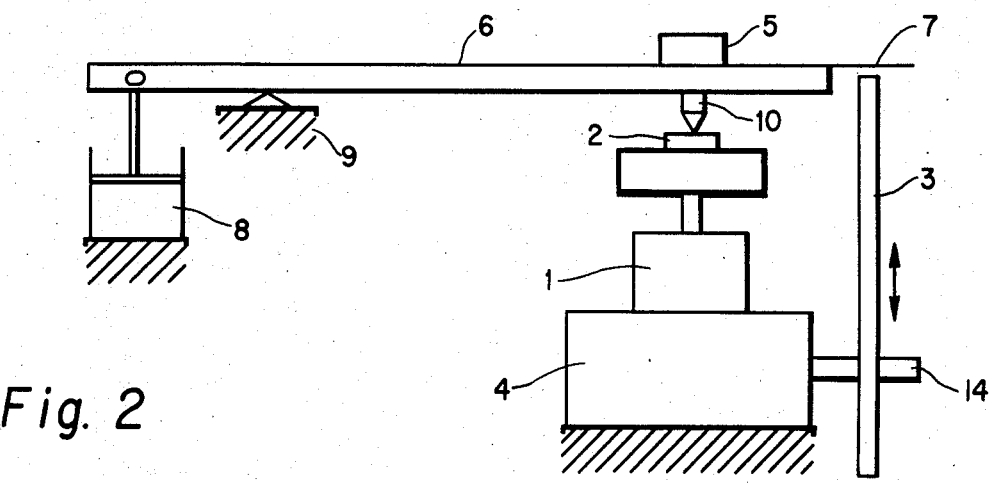
FIG. 2 illustrates diagramatically one embodiment of the invention.
Figure 3:
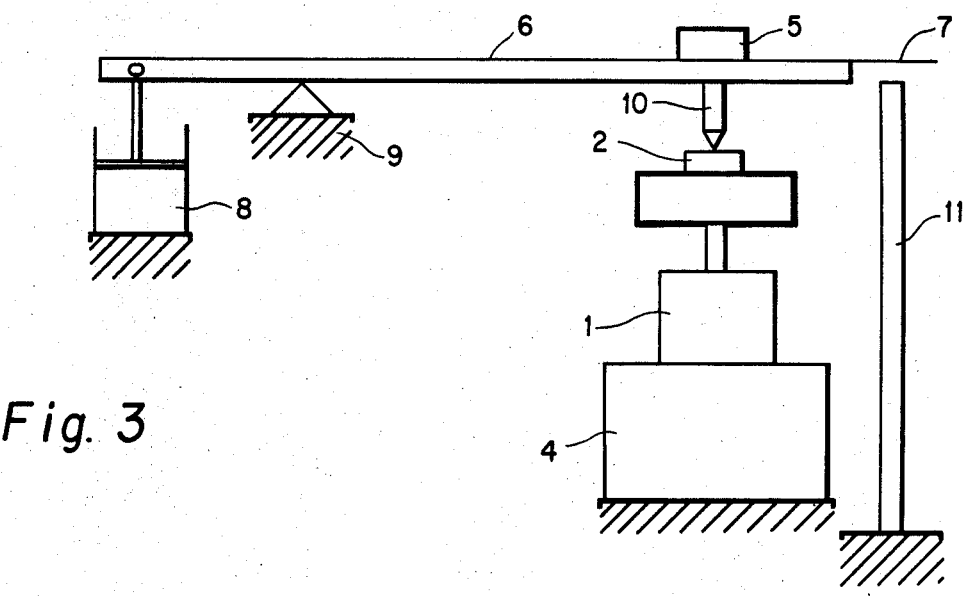
FIG. 3 illustrates a second embodiment of the invention.
Figure 4:
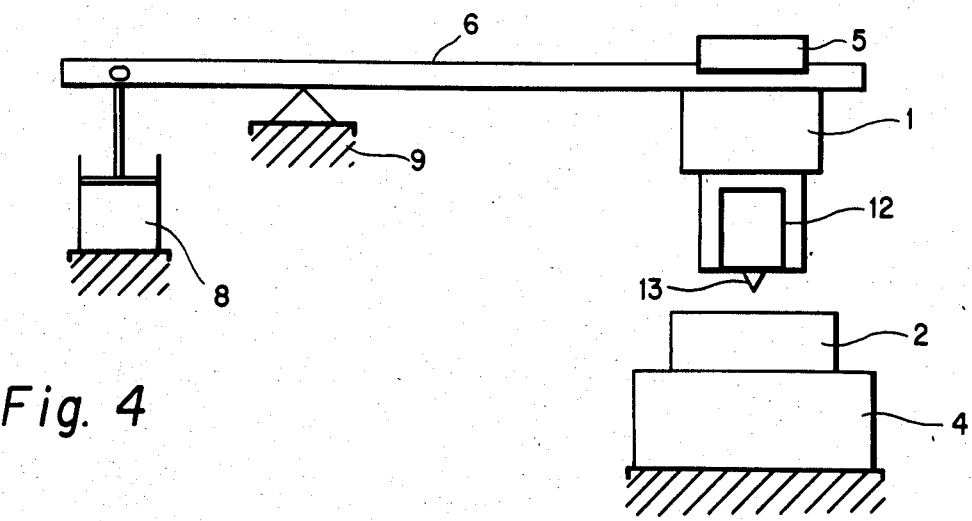
FIG. 4 illustrates a third embodiment of the invention.

FIG. 1 illustrated schematically the essential elements of the present invention and there interrelationship, while FIGS. 2, 3, and 4 illustrate three alternative embodiments of the device of the invention.

In FIG. 2 of the drawings, one embodiment of the present invention is shown in which the load cell 1, which must be essentially incompressible, is mounted on the stage 4 directly under the sample 2 and a capacitor probe 3 such as described in U.S. Pat. No. 4,067,255 is mounted on a base 14 attached to the stage 4. A reference arm 7 projects from the end of the arm 6 and is disposed directly over the capacitor probe 3 which can be adjusted vertically to accommodate samples of different thickness. Since the capacitor probe 3 and the sample 2 are both connected with the stage 4, any vertical movement of the sample will be reflected in a similar vertical movement in the capacitor probe. Lateral movement of the sample on the stage, however, is independent of the capacitor probe.

In accordance with the use of the present invention, the sample 2 is brought within the range of vertical displacement of the diamond indenter 10 using a microscope for sighting which is aligned with the indenter. The capacitor probe for sensing vertical displacement of the arms 6 and 7 is then readjusted in height so that the cell displacement occurs within its linear range. An actuating mechanism 8, which is conventional, is used to initiate and control vertical downward displacements of the diamond stylus 10. During the indentation process, data is fed into a micro-computer with a very fast A/D converter which also serves as clock mechanism for measuring the time. This embodiment of the present invention has the advantage that it is easy to fabricate; however, it requires readjusting the capacitor probe calibration each time a sample is changed.

Directing attention to FIG. 3 of the drawings, an alternative embodiment of the present invention is shown in which the capacitor probe 11 for sensing vertical displacement of the diamond stylus 10 is not connected to the stage 4 but is independently attached to the instrument housing (not shown) itself. The advantage of this embodiment of the present invention is that it provides a very strong, inflexible mounting for the probe which results in less scatter of data. On the other hand, this embodiment is somewhat more difficult to fabricate and does not compensate for errors or displacements occurring below the load cell.

In FIG. 4 of the drawings, the load cell 1 is mounted directly under the arm 6 and the load 5 and above the capacitance probe 12 which is mounted in line with the indenter 13. Accordingly, the reference surface instead of being a projecting arm 7 as shown in FIGS. 2 and 3 is the metallic sample surface itself 2. This embodiment of the present invention allows exact compensation for any displacement in the system other than those which are of interest. It further allows the use of a load cell which is soft, i.e. can be displaced somewhat as the load is applied, in contrast to the essentially incompressible piezo-electric type typically used in the previously described embodiments of the present invention. This is because the various geometrical arrangements measure only displacements between the sample and the probe surface.

Figure 5:
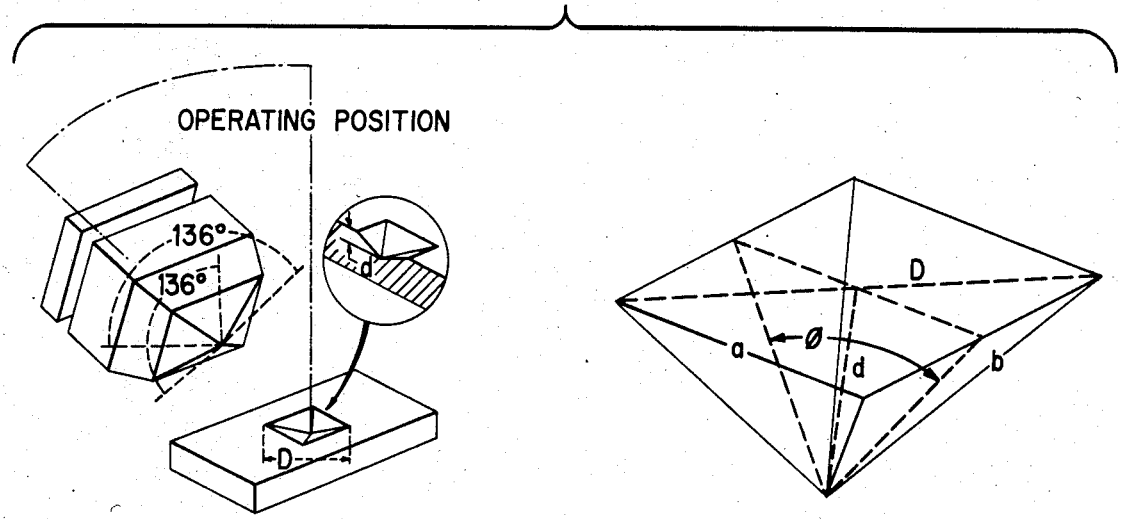
FIG. 5 illustrates the geometric configuration of a Vickers diamond stylus.
Figure 6:
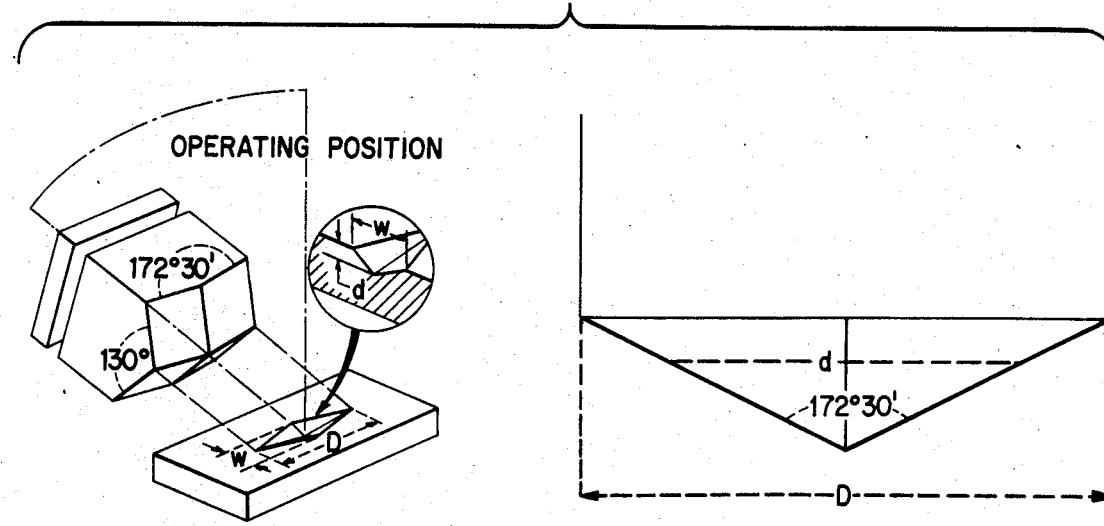
FIG. 6 illustrates the geometric configuration of a Knoop diamond stylus.
Figure 7:
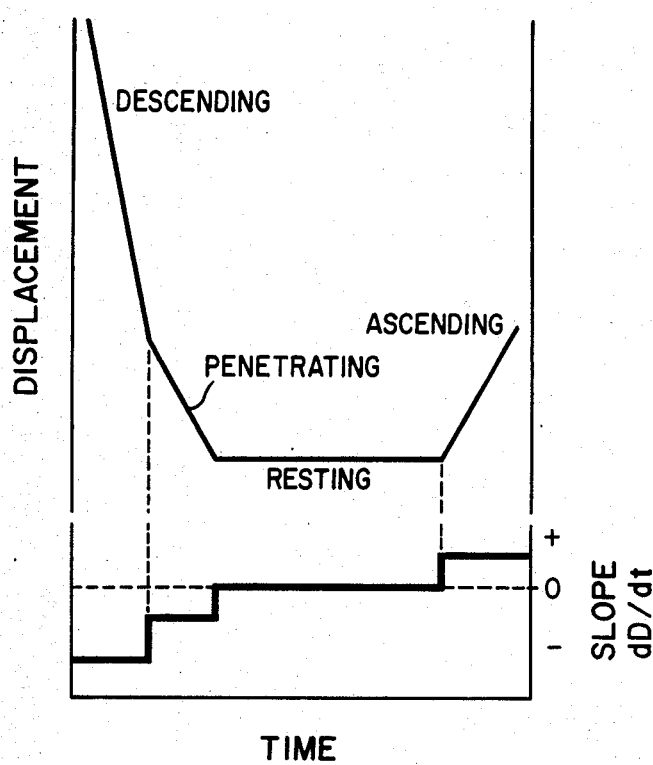
FIG. 7 is a differential time-displacement curve.

In order to measure hardness of a material in accordance with the present invention the applied load and displacement into the sample of the diamond stylus must be determined. To determine displacement, the time when the indenter first strikes the surface of the material must be determined and this is obtained by taking the differential dD/dt of a displacement-time curve such as shown in FIG. 7 of the drawings. FIGS. 5 and 6 of the drawings illustrate the geometrical properties of respective diamond styli and from this information it becomes possible to calculate the hardness:

For hardness (HV) using a Vickers diamond as shown in FIG. 5:

$$HV = \frac{2L \sin \theta/2}{D^2}$$

$$D = a\sqrt{2}$$

$$\TAN 68° = \frac{a/2}{d} = \frac{a}{2d}$$

$$a = \TAN 68° (2d)$$

$$a = 4.9502 (d)$$

$$D = 4.9502 (d)\sqrt{2}$$

$$D = 7.0006 (d); d - \text{Displacement}$$

therefore:

$$HV = \frac{2 L \sin 68°}{(7.0006)^2(d)^2}$$

And for hardness (HK) using a Knoop diamond as shown in FIG. 6:

$$HK = \frac{L}{C D^2}$$

$$\TAN 86° 15' = \frac{D/2}{d} = \frac{D}{2d}$$

$$D = \TAN 86° 15' (2d)$$

$$D = 30.5141 (d); d = \text{Displacement}$$

therefore:

$$HK = \frac{L}{C(30.5141)^2(d^2)}$$

FIGS. 5 and 6 also show the relationship between the optically measured distance (D) or width of the indentation and the depth of penetration (d). By knowing these relationships and the Load, the microhardness can be calculated.

Hardness values obtained using this procedure do not take into account the elastic portion of the relaxation but can be used for large loads or for materials in which it is known that the elastic portion of the displacement is relatively small compared with the anelastic portion.

Figure 9:
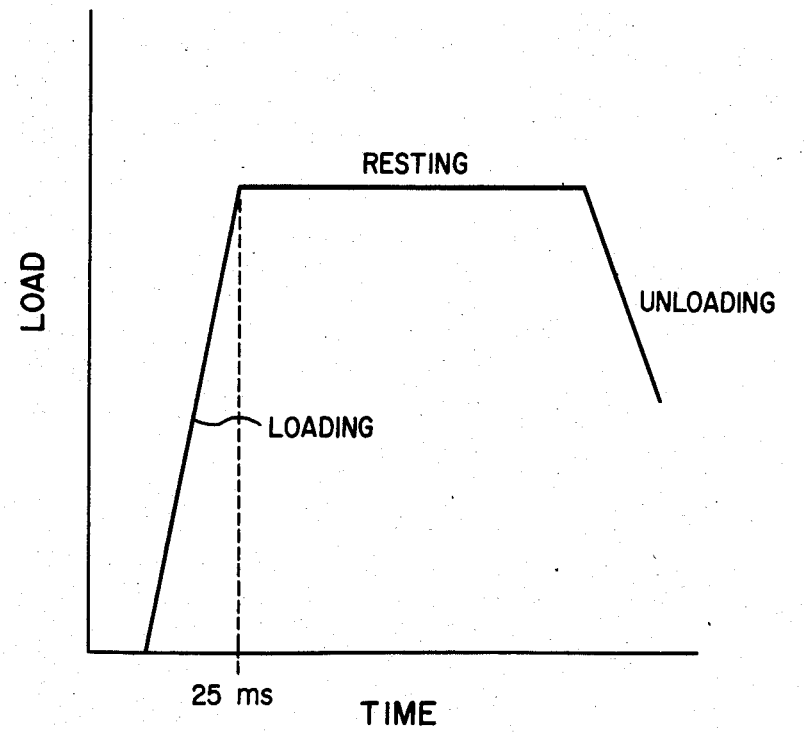
FIG. 9 is a curve of load vs. time.
Figure 8:
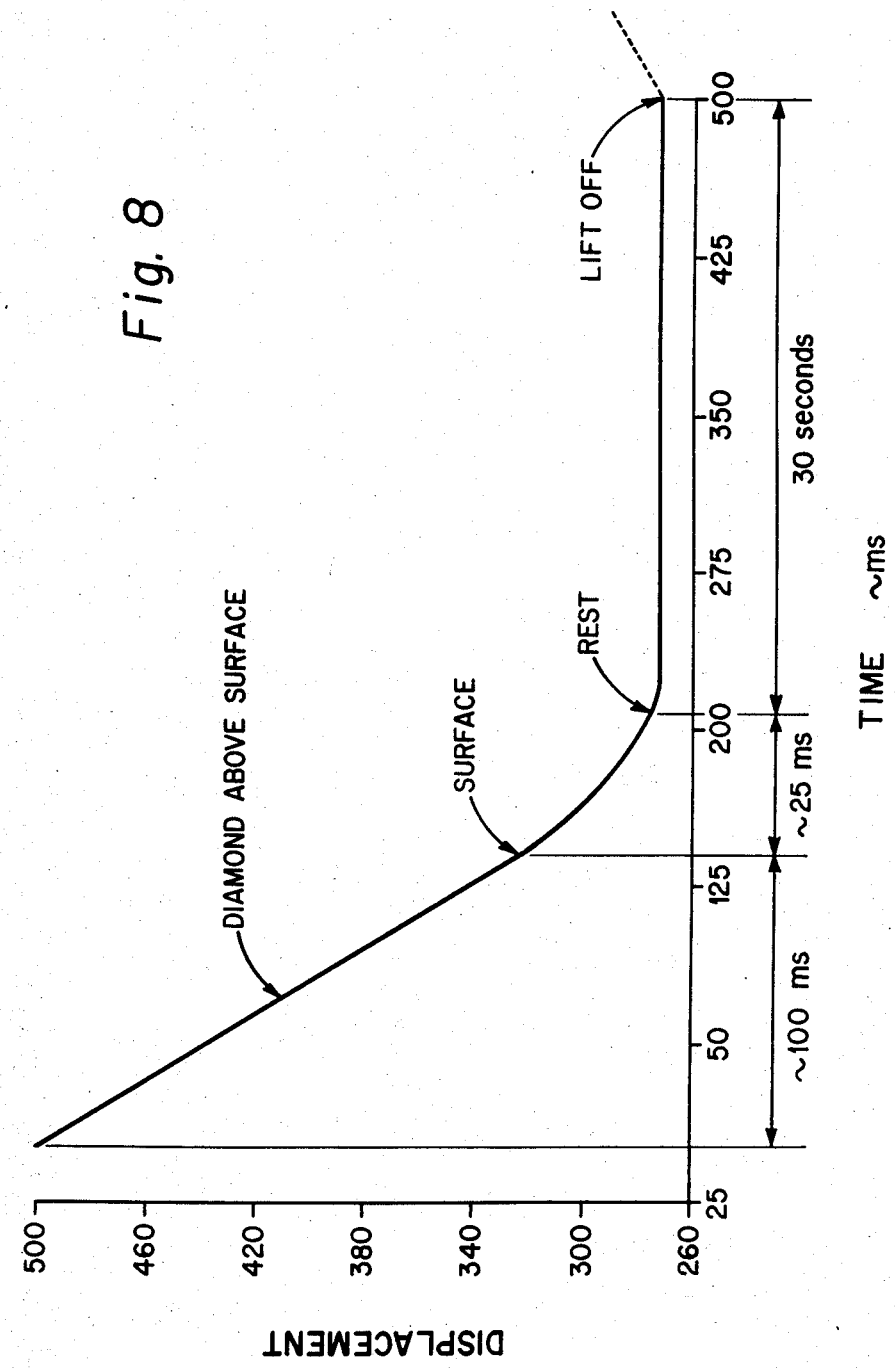
FIG. 8 is a further curve of time vs. displacement.

FIG. 8 of the drawings shows an example of a typical displacement-time characteristic using the device of the present invention. The corresponding load-time curve is shown in FIG. 9 and the load plotted as a function of displacement is shown in FIG. 10 (for fine grain polycrystalline copper). Also indicated in FIG. 10 are the elastic and anelastic portions of the data.

By way of comparison with the present invention, optical equivalent hardness values were obtained by measuring elastic contraction and using the result of displacement in the Vickers and Knoop equations. A comparison of data obtained using the conventional optical system and the automated system of the present invention can be seen in FIG. 12 which illustrates relative scatter.

Hardness-depth curves yield not only information on near surface material properties but also can provide information on work hardening and elastic properties. For example, in FIG. 11, similar curves for fine grain polycrystalline copper are displayed together. An indication of the elastic moduli can also be obtained from the instantaneous value of the slope of the hardness-displacement curves at the moment of unloading.

It will be appreciated by those skilled in the art that variations in instrumentation can be practiced within the scope of the present invention. For example, displacement can be measured using, in addition to a capacitor probe, an eddy current meter, a magnetic probe, a linear differential transducer or an optical interferometric device such as a Fabry-Perot interferometer with a fringe counter. Other variations in both the practice and instrumentation of the invention will be apparent and are considered to fall within the scope of the invention as described herein and defined in the appended claims.

What is claimed is:

1. A device to aid in measuring and evaluating mechanical properties of a material comprising:
    (a) a stage for holding an essentially flat sample of said material;
    (b) a stylus mounted on one end of a lever arm to vertically impinge on said sample when said stylus is displaced downward;
    (c) a load mounted on said lever arm above said stylus;
    (d) actuating means for controlling said downward displacement of said stylus;
    (e) means for simultaneously measuring time of said displacement, distance of said displacement and load being applied to said stylus when impinging on said sample;
    (f) means for receiving and correlating signals generated by said measuring means to produce values relating to mechanical properties of said material.

2. The device of claim 1 wherein said means for measuring downward displacement of the stylus is a capacitor.

3. The device of claim 2 wherein said means for measuring load is a load cell disposed on said stage.

4. The device of claim 2 wherein said means for measuring load is a load cell disposed on said lever arm in vertical alignment with said load, said capacitor and said stylus.

5. The device of claim 4 wherein said capacitor is disposed immediately adjacent said stylus and said load cell is disposed between said capacitor and said lever arm.

6. The device of claim 1 wherein said means for measuring downward displacement registers deflection of said lever arm.

7. The device of claim 1 wherein said means for measuring downward displacement is mounted on said stage.

8. The device of claim 1 wherein said means for measuring downward displacement is mounted independently of said stage.

9. The device of claim 1 wherein said means for measuring load is a load cell disposed on said stage.

10. The device of claim 1 wherein said material is a metal.

11. The device of claim 1 wherein the mechanical properties which said device aids in the evaluation of are hardness, elastic modulus, stress-strain, wear, fatigue, plastic deformation and tensile strength.

12. A device for measuring and evaluating the hardness of a metal comprising:
- (a) a stage for holding an essentially flat sample of said metal;
- (b) a diamond stylus mounted to one end of a lever arm to vertically impinge on said metal when said stylus is displaced downward;
- (c) a load mounted on said lever arm above said stylus;
- (d) acutating means for initiating and controlling said downward displacement of the stylus;
- (e) means for measuring the time of said displacement;
- (f) load cell means for measuring the load being applied to said stylus when impinging on said metal; and means for measuring the vertical displacement of said stylus;
- (g) means for receiving and correlating signals generated by said measuring means to produce values relating to the hardness of said material.

* * * * *